(12) United States Patent
Amiche et al.

(10) Patent No.: US 6,521,214 B1
(45) Date of Patent: Feb. 18, 2003

(54) PROCESS FOR PREPARATION OF ABRASIVE PRECIPITATED SILICA

(75) Inventors: Frèdèric Amiche, Aulnay-Sous-Bois (FR); Adrien Dromard, Lyons (FR); Yvonick Chevallier, Fontaines Saint Martin (FR)

(73) Assignee: Rhone-Poulenc Chimie, Courbevoie Cedex (FR)

( * ) Notice: Subject to any disclaimer, the term of this patent is extended or adjusted under 35 U.S.C. 154(b) by 339 days.

(21) Appl. No.: 09/659,745

(22) Filed: Sep. 11, 2000

Related U.S. Application Data

(63) Continuation of application No. 09/214,419, filed as application No. PCT/FR97/01207 on Jul. 4, 1997, now abandoned.

(30) Foreign Application Priority Data

Jul. 5, 1996 (FR) .............................. 96 08383

(51) Int. Cl.⁷ .............................. A61K 7/10; C01B 33/12
(52) U.S. Cl. ........................ 424/49; 51/308; 423/335; 423/339
(58) Field of Search .................. 423/435, 439; 424/49–58

(56) References Cited

U.S. PATENT DOCUMENTS

| | | | |
|---|---|---|---|
| 4,067,746 A | * 1/1978 | Wason et al. ................ 423/339 |
| 4,590,052 A | * 5/1986 | Chevallier et al. .......... 423/335 |
| 4,618,488 A | * 10/1986 | Maeyama et al. ............. 424/49 |
| 4,708,859 A | * 11/1987 | Chevallier ................... 423/339 |
| 4,842,838 A | * 6/1989 | Chevallier ................... 423/339 |
| 4,874,594 A | * 10/1989 | Chevallier ................... 423/335 |
| 4,992,251 A | * 2/1991 | Aldcroft et al. ............. 423/335 |
| 5,035,879 A | * 7/1991 | Aldcroft et al. ............... 424/49 |
| 5,279,815 A | * 1/1994 | Wason et al. ................. 424/52 |
| 5,395,605 A | * 3/1995 | Billion et al. ............... 423/339 |
| 5,403,570 A | * 4/1995 | Chevallier et al. .......... 423/339 |
| 5,512,271 A | * 4/1996 | McKeown et al. ............ 424/49 |
| 5,932,191 A | * 8/1999 | Chevallier et al. ............. 424/52 |
| 5,964,937 A | * 10/1999 | Stanier ....................... 423/339 |
| 6,001,322 A | * 12/1999 | Chevallier et al. .......... 423/339 |
| 6,107,226 A | * 8/2000 | Chevallier ................... 501/133 |
| 6,169,135 B1 | * 1/2001 | Chevallier et al. .......... 423/335 |
| 6,187,292 B1 | * 2/2001 | Amiche et al. ............... 424/49 |
| 6,290,924 B1 | * 9/2001 | Chevallier ................... 423/335 |
| 6,335,396 B1 | * 1/2002 | Chevallier et al. .......... 423/335 |
| 6,399,111 B1 | * 6/2002 | Stanier ....................... 423/339 |

* cited by examiner

*Primary Examiner*—Shep K. Rose
(74) *Attorney, Agent, or Firm*—Burns, Doane, Swecker & Mathis, L.L.P.

(57) ABSTRACT

A process for the preparation of precipitated silica is disclosed. The precipitated silica has a refractive index from about 1.440 to about 1.450, among other properties. The silica is prepared by a method including; a first step of using an initial feedstock of water, an electrolytic salt and a fraction of the total amount of silicate employed; a second step including preneutralizing the feedstock with the acidifying agent until about 50 to 85% of the amount of $M_2O$ present has been neutralized; a third step including introducing into the preneutralized feedstock the remaining fraction of alkali metal silicate in aqueous solution and the acidifying agent, under conditions such that the pH of the reaction medium remains substantially constant and from about 8.6 to about 9.6; a fourth step including, after the addition of silicate is stopped, in continuing the addition of acidifying agent until the medium reaches a pH of about 7 to 8; a fifth step including, after maturation, in continuing the acidification of the reaction medium until a silica broth with a pH of about 3.7 to 4.6 is obtained; wherein the consolidation ratio CR $$CR = \frac{\text{Total amount of silicate employed, expressed as } SiO_2}{\text{Total amount of silicate in the feedstock, expressed as } SiO_2}$$

of the process is less than or equal to 7, and the separated and dried silica is ground, if necessary, until an average particle diameter $d_{50}$ from about 6 to about 13 $\mu$m is obtained.

2 Claims, No Drawings

PROCESS FOR PREPARATION OF ABRASIVE PRECIPITATED SILICA

This application is a continuation, of application Ser. No. 09/214,419, filed Mar. 17, 1999 now abandoned which is a filing under 35 U.S.C. §371 of International Application No. PCT/FR97/01207 filed on Jul. 4, 1997.

The present invention relates to an abrasive precipitated silica which can be used in particular in toothpaste compositions, to a process for its preparation, to its use in toothpaste compositions, especially those for frequent use, and to toothpaste compositions comprising the said silica.

Highly abrasive silicas are usually used in toothpaste compositions on account of the high-quality cleaning power which they give to the said compositions; however, on account of the risks of damage which such silicas can cause to oral tissues by frequent brushing, it is desired to have silicas which are less abrasive than the standard toothpaste silicas while at the same time retaining high cleaning power in formulation.

The applicant has found a silica which solves this problem.

A first subject of the invention consists of a precipitated silica which can be used as an abrasive agent in toothpaste compositions, the silica having

- a BET specific surface from about 60 to about 150 $m^2/g$, preferably from about 70 to about 130 $m^2/g$
- an RDA abrasiveness from about 30 to about 90, preferably from about 40 to about 80, most particularly from about 40 to about 70
- a refractive index from about 1.440 to about 1.450
- a DOP oil uptake from about 115 to about 170 ml/100 g, preferably from more than 120 ml/10 g to about 170 ml/100 g, and
- an average particle diameter $d_{50}$ from about 6 to about 13 $\mu$m, most particularly from about 7 to about 12 $\mu$m.

The said silica has a CTAB specific surface from about 20 to about 80 $m^2/g$, preferably from about 30 to about 60 $m^2/g$.

The BET specific surface is determined according to the Brunauer-Emmett-Teller method described in "The journal of the American Chemical Society", Vol. 60, page 309, February 1938 and corresponding to NFT standard 45007 (November 1987).

The CTAB specific surface is the external surface area determined according to NFT standard 45007 (November 1987) (5.12).

The RDA ("radioactive dentine abrasion") abrasiveness is measured according to the method described by J. J. Hefferren in "Journal of Dental Research", Vol. 55(4), pages 563–573, 1976.

According to this method, human teeth irradiated with a flow of neutrons are subjected to a certain amount of mechanical brushing; the abrasion index of the silica tested corresponds to the $^{32}p$ radioactivity emanating from the dentine. A suspension containing 10 grams of calcium pyrophosphate dispersed in 50 ml of a 90/10 by volume water/glycerol solution containing 0.5% of sodium carboxymethylcellulose is selected as reference, the RDA value of this reference being arbitrarily set at 100. The silica whose RDA it is desired to measure is placed in suspension like the calcium pyrophosphate and subjected to the same mechanical brushing.

The DOP oil uptake is determined according to ISO standard 787/5 using dioctyl phthalate.

The refractive index measured in sorbitol is that of the most transparent suspension (thus the suspension with the maximum transmission) of this silica in various water/sorbitol solutions, this transparency being determined by transmission at 589 nm with a spectrophotometer. Each suspension is obtained by dispersing one gram of silica in 19 grams of water/sorbitol solution, followed by de-aeration under a gentle vacuum, before reading the transmission (reading carried out with the silica-free water/sorbitol solution as reference product) on the spectrophotometer and the refractive index on a refractometer.

The weight-average diameter $d_{50}$ of the silica particles is determined using a Sympatec Helos machine. This machine applies the principle of Fraunhoffer scattering and uses a low-power He/Ne laser. The sample is predispersed in water by applying ultrasound for 30 seconds in order to obtain an aqueous suspension.

A second subject of the invention consists of process for preparing the said silica.

According to this second subject of the invention, it is a process for preparing precipitated silica by reaction of an alkali metal M silicate, with an $SiO_2/M_2O$ ratio from about 2 to about 4, preferably from about 3 to about 3.8, with an acidifying agent, optional maturation of the silica broth formed, separation and drying of the silica suspension recovered and optional grinding, the operation for formation of the silica broth being carried out according to the following steps:

first step consisting in using an initial feedstock consisting of water, an electrolytic salt and a fraction of the total amount of silicate employed;

a second step consisting in preneutralizing the said feedstock with the acidifying agent until about 50 to 85% of the amount of $M_2O$ present has been neutralized;

a third step consisting in introducing into the said preneutralized feedstock the remaining fraction of alkali metal silicate in aqueous solution and the acidifying agent, under conditions such that the pH of the reaction medium remains substantially constant and from about 8.6 to about 9.6;

a fourth step consisting, after the addition of silicate is stopped, in continuing the addition of acidifying agent until the medium reaches a pH of about 7 to 8;

a fifth step consisting, after maturation, in continuing the acidification of the reaction medium until a silica broth with a pH of about 3.7 to 4.6 is obtained;

the said process being characterized in that the consolidation ratio CR $$CR = \frac{\text{Total amount of silicate employed, expressed as } SiO_2}{\text{Total amount of silicate in the feedstock, expressed as } SiO_2}$$

is less than or equal to 7, preferably from about 4 to about 6.5, and in that the separated and dried silica is ground, if necessary, until an average particle diameter $d_{50}$ from about 6 to about 13 $\mu$m, preferably from about 7 to about 12 $\mu$m, is obtained.

The silicate and the acidifying agent for carrying out the process of the invention are chosen in a manner which is well known per se.

The alkali metal silicate is advantageously a sodium or potassium silicate. Sodium silicates can be mentioned most particularly.

The said silicate is used in the form of an aqueous solution with a concentration, expressed as $SiO_2$, from about 50 to about 350 g/l, preferably from about 100 to about 250 g/l.

A strong inorganic acid such as sulphuric acid, nitric acid or hydrochloric acid, or an organic acid such as acetic acid, formic acid or carbonic acid is generally used as acidifying agent. It is preferably sulphuric acid. This acid can be used in dilute or concentrated form, preferably in the form of an aqueous solution with a concentration from about 40 to about 400 g/l, preferably from about 60 to about 400 g/l.

Among the electrolytes which can be mentioned in particular are alkali metal or alkaline-earth metal salts, in particular the metal salt of the starting silicate and of the acidifying agent, i.e., preferably, sodium sulphate; sodium chloride, nitrate and hydrogen carbonate are also advantageous.

The first step consists in forming the feedstock consisting of water, at least one electrolytic salt and a fraction of the total amount of silicate.

The silicate concentration in the initial feedstock is from about 10 to about 100 g, preferably from about 25 to about 90 g, of $SiO_2$ per litre of feedstock.

The amount of electrolytic salt present in the feedstock can be from about 0.05 to about 0.3 mol/litre when it is an electrolytic salt of an alkali metal or from about 0.005 to about 0.05 mol/litre when it is an electrolytic salt of an alkaline-earth metal.

The feedstock obtained is brought to a temperature from about 70 to about 98° C., preferably from about 80 to about 95° C., and is kept stirring.

The second step consists in adding, under the same conditions, acidifying agent to the said initial feedstock, until from about 50 to about 85%, preferably from about 55 to about 80%, of the amount of $M_2O$ present has been neutralized.

The third step consists in adding to the preneutralized feedstock, which is kept stirring, the remaining fraction,of silicate solution and the acidifying agent simultaneously.

The respective amounts of alkali metal silicate and of acidifying agent are chosen so as to keep the pH of the reaction medium at a more or less constant value of about 8.6 to 9.6, preferably of about 9 to 9.4, throughout the introduction of the two reagents.

These two solutions are introduced while keeping the medium at a temperature from about 70 to about 98° C., preferably from about 80 to about 95° C.

Introduction of the silicate solution is then stopped in order to obtain a consolidation ratio CR, as defined above, of less than or equal to 7, preferably from about 4 to about 6.5.

This third step generally lasts from about 20 to about 50 minutes.

The fourth step is carried out by continuing the addition of acidifying agent to the reaction medium with stirring, under the same temperature conditions, until the medium reaches a pH of about 7 to 8, preferably of about 7.3 to 7.8.

The medium is then left to mature under the same temperature conditions, for about 5 to 30 minutes, preferably for about 5 to 10 minutes, before reintroducing the acidifying agent in order to carry out the fifth step, until the medium (acidified broth) reaches a pH of about 3.7 to 4.6, preferably of about 3.9 to 4.5.

At the end of the fifth step, after totally stopping the addition of acidifying agent, the reaction medium is left to mature under the same temperature conditions. This maturation operation can last from about 5 to about 30 minutes, preferably from about 5 to about 10 minutes.

After the operations described above, a silica broth is obtained, which is then separated (liquid-solid separation); this operation generally consists of a filtration (for example using a rotary filter under vacuum), followed by washing with water. A silica suspension (filter cake) is thus recovered, which is then dried, preferably by spraying (for example turbomixer sprayer).

The silica thus obtained is ground, if necessary, until an average particle diameter $d_{50}$ from about 6 to about 13 $\mu$m, preferably from about 7 to about 12 $\mu$m, is obtained.

The silica forming the subject of the invention, which can be obtained according to the process described above, has the advantage, on incorporation into a toothpaste composition, of giving the said toothpaste composition a low or moderate abrasive power without any risk of damage to oral tissues, while at the same time providing cleaning power which is sufficient to efficiently remove dental plaque and the various types of debris. This silica is thus most particularly suitable for the formulation of toothpastes for frequent use.

The RDA abrasive power of the toothpastes is also determined according to the method described by J. J. Hefferren in "Journal of Dental Research", Vol. 55(4), pages 563–573, 1976, using 25 g of toothpaste.

The cleaning power of the toothpastes is determined according to the method described by G. K. Stookey, T. A. Burkhard and B. R. Schemehorn in "Journal of Dental Research", Vol. 61, No. 11, November 1982, pages 1236–1239.

A subject of the present invention is also the use of the above silica as an abrasive agent in toothpaste compositions, as well as the toothpaste compositions comprising the said silica.

The said silica can be present in the said toothpaste compositions in a proportion of about 5 to about 50%, preferably from about 5 to about 30%, of the weight of the said compositions.

The toothpaste compositions forming the subject of the invention generally have an RDA abrasiveness, measured as indicated above, of less than 55 for an amount of silica of the invention of about 10 g per 100 g of paste, with a cleaning power/RDA ratio of greater than 1, preferably greater than 1.5.

These compositions can also contain other common ingredients, in particular other water-insoluble mineral abrasive agents, thickeners, wetting agents, etc.

As other abrasive agents, mention may be made in particular of calcium carbonate, hydrated alumina, bentonite, aluminum silicate, zirconium silicate, and sodium, potassium, calcium and magnesium metaphosphates and phosphates. The total amount of abrasive powder(s) can constitute from about 5 to about 50% of the weight of the dental composition.

Among the thickeners, mention may be made most particularly of thickening silicas in an amount is from about 1 to about 15% of the weight [lacuna], xanthan gum, guar gum, carrageenans, cellulose derivatives, alginates, in an amount which can range up to 5% of the weight of the said composition, etc.

Among the wetting agents, mention may be made, for example, of glycerol, sorbitol, polyethylene glycols, polypropylene glycols and xylitol, in an amount from about 2 to about 85%, preferably from about 10 to about 70%, of the weight of toothpaste composition expressed as solids.

These toothpaste compositions can also contain surfactants, detergents, dyes, antibacterial agents, fluoro derivatives, opacifiers, flavourings, sweeteners, antitartar agents, antiplaque agents, bleaching agents, sodium bicarbonate, antiseptics, enzymes, natural extracts (camomile, thyme, etc.), etc.

The examples which follow are given for illustrative purposes.

EXAMPLE 1

Preparation of the Feedstock

The following are introduced into a 25-litre reactor:

2.2 litres of mains water 966 g of an aqueous sodium silicate solution with an $SiO_2/Na_2O$ ratio of 3.5, containing 135 g/l of $SiO_2$ 72 g of sodium sulphate.

The temperature is brought to 90° C. with vigorous stirring.

Preneutralization

A sulphuric acid solution at 80 g/l is then added, under the same conditions, until the feedstock is 71% neutralized.

Simultaneous Addition

An aqueous sodium silicate solution with an $SiO_2/Na_2O$ ratio of 3.5, containing 135 g/l of $SiO_2$, and an aqueous solution containing 80 g/l of sulphuric acid are then introduced simultaneously over 30 minutes, so as to reach a more or less-constant pH of 9–9.2, and until a consolidation ratio CR of 6.2 is obtained.

1st Acidification

After stopping the introduction of silicate, the addition of sulphuric acid solution is continued under the same conditions, until a pH of 7.5 is obtained.

Maturation

The addition of acid is stopped and the reaction medium is left to mature for 5 minutes under the same temperature conditions.

2nd Acidification

The sulphuric acid solution is again introduced, under the same conditions, until a pH of 4.2 is obtained.

The product is then filtered, washed and spray-dried.

The characteristics of the product obtained are given in Table 1.

EXAMPLE 2

Preparation of the Feedstock

The following are introduced into a 2 m³ reactor:

94 litres of mains water 125 litres of an aqueous sodium silicate solution with an $SiO_2/Na_2O$ ratio of 3.5, containing 135 g/l of $SiO_2$ 4 kg of sodium sulphate, which corresponds to 77 g/litre of $SiO_2$ and 18.3 g/litre of sodium sulphate in the feedstock.

The temperature is brought to 92° C. with vigorous stirring.

Preneutralization

A sulphuric acid solution at 80 g/l is then added, under the same conditions, until the feedstock is 71% neutralized.

Simultaneous addition

An aqueous sodium silicate solution with an $SiO_2/Na_2O$ ratio of 3.5, containing 135 g/l of $SiO_2$, and an aqueous solution containing 80 g/l of sulphuric acid are then introduced simultaneously over 40 minutes, so as to reach a more or less constant pH of 9–9.2, and until a consolidation ratio CR of 7 is obtained.

1st acidification

After stopping the introduction of silicate, the addition of sulphuric acid solution is continued under the same conditions, until a pH of 7.5 is obtained.

Maturation

The addition of acid is stopped and the reaction medium is left to mature for 5 minutes under the same temperature conditions.

2nd acidification

The sulphuric acid solution is again introduced, under the same conditions, until a pH of 4.2 is obtained.

The product is then filtered, washed, spray-dried and ground.

The characteristics of the product obtained are given in Table 1.

EXAMPLES 3–5

The operations described in Example 2 are repeated with the modifications featured in Table 1. The characteristics of the products obtained are given in Table 1.

Comparative Examples 6 and 7

The operations described in Example 2 are repeated with the modifications featured in Table 1. The characteristics of the products obtained are given in Table 1.

Examples 1 to 5 above, carried out with a consolidation ratio CR of up to 7, show that the RDA abrasiveness of the silicas obtained is not more than 75, whereas the use of a consolidation ratio CR of 8 (Comparative Examples 6 and 7) leads to silicas with an RDA abrasiveness of at least 97.

EXAMPLES 8–10

The silicas of Comparative Examples 2, 4 and 7 are used as abrasive agent in the preparation of toothpaste, the composition of which is given in Table 2.

The RDA abrasive power and the cleaning power of these pastes are featured in Table 2.

It is observed that the cleaning power of the pastes containing lot of their weight of silica of the invention (silica of Examples 2 and 4) is at least as high as that of the pastes containing the same amount of standard silica; the cleaning power/RDA ratio of the pastes according to the invention is thus particularly high.

TABLE 1

| | Example | | | | | | |
|---|---|---|---|---|---|---|---|
| Process | 1 | 2 | 3 | 4 | 5 | 6 comparative | 7 comparative |
| Feedstock | | | | | | | |
| Water (litres) | 2.2 | 94 | 101 | 101 | 101 | 78 | 78 |
| Silicate (litres) | 0.85 | 125 | 148 | 135 | 135 | 104 | 104 |
| Sodium sulphate (kg) | 0.072 | 4 | 5.6 | 5.6 | 5.6 | 1.1 | 4.3 |
| $SiO_2$ (g/l) | 38 | 77 | 80 | 77 | 77 | 77 | 77 |
| Sodium sulphate (g/l) | 24 | 18.3 | 22.5 | 23.7 | 23.7 | 6 | 23.6 |

TABLE 1-continued

| | Example | | | | | | |
|---|---|---|---|---|---|---|---|
| Process | 1 | 2 | 3 | 4 | 5 | 6 comparative | 7 comparative |
| Preneutralization | | | | | | | |
| Content (%) | 71 | 71 | 65 | 72 | 57 | 71 | 71 |
| Simultaneous addition | | | | | | | |
| CR | 6.2 | 7 | 5.6 | 6 | 5.25 | 8 | 8 |
| Duration (minutes) | 30 | 40 | 40 | 40 | 41.5 | 40 | 40 |
| Characteristics | | | | | | | |
| BET (m²/g) | 109 | 112 | 89 | 73 | 83 | 91 | 70 |
| CTAB (m²/g) | 32 | 43 | 42 | 44 | 48 | 36 | 35 |
| DOP (ml/100 g) | 146 | 122 | 140 | 137 | 151 | 120 | 96 |
| RDA | 68 | 75 | 62 | 66 | 51 | 97 | 125 |
| IR | 1.445 | 1.445 | 1.445 | 1.445 | 1.446 | 1.444 | 1.442 |
| $d_{50}$ (μm) | 8.3 | 9.1 | 9.1 | 8.5 | 8.3 | 9.3 | 9.1 |

TABLE 2

| Formulation | | | |
|---|---|---|---|
| Sorbitol (70% solution) | 49% | 49% | 49% |
| Silica of Example 2 | 10% | | |
| Silica of Example 4 | | 10% | |
| Silica of Example 7 | | | 10% |
| Tixosil 43 thickening silica | 9% | 9% | 9% |
| Sodium lauryl sulphate | 1.3% | 1.3% | 1.3% |
| Titanium dioxide | 1% | 1% | 1% |
| Sodium benzoate | 0.2% | 0.2% | 0.2% |
| Sodium carboxymethylcellulose | 0.9% | 0.9% | 0.9% |
| Sodium saccharinate | 0.2% | 0.2% | 0.2% |
| Sodium fluoride | 0.24% | 0.24% | 0.24% |
| Flavouring | 1% | 1% | 1% |
| Deionized water (qs 100%) | 27.16% | 27.16% | 27.16% |
| Characteristics | | | |
| RDA | 42 | 38 | 70 |
| Cleaning power (%) | 75 | 63 | 73 |
| Cleaning power/RDA | 1.79 | 1.66 | 1.04 |

What is claimed is:

1. Process for the preparation of precipitated silica with a BET specific surface from about 60 to about 150 m²/g, an RDA abrasiveness from about 30 to about 90, a refractive index from about 1.440 to about 1.450 a DOP oil uptake from about 115 to about 170 ml/100 g, and an average particle diameter $d_{50}$ from about 6 to about 13 μm, by reaction of an alkali metal M silicate, with an SiO₂/M2O ratio from about 2 to about 4, with an acidifying agent, optional maturation of the silica broth formed separation and drying to the silica suspension recovered and optional grinding, the operation for formation of the silica broth being carried out according to the following steps:

a first step comprising using an initial feedstock consisting of water, an electrolytic salt and a fraction of the total amount of silicate employed;

a second step comprising preneutralizing said feedstock with the acidifying agent until about 50 to 85% of the amount of M₂O present has been neutralized;

a third step comprising introducing into said preneutralized feedstock the remaining fraction of alkali metal, silicate in aqueous solution and the acidifying agent, under conditions such that the pH of the reaction medium remains substantially constant and from about 8.6 to about 9.6;

a fourth step comprising, after the addition of silicate is stopped, in continuing the addition of acidifying agent until the medium reaches a pH of about 7 to 8;

a fifth step comprising, after maturation, in continuing the acidification of the reaction medium until a silica broth with a pH of about 3.7 to 4.6 is obtained;

wherein the consolidation ratio CR $$CR = \frac{-\text{Total amount of silicate employed, expressed as SiO}_2}{\text{Total amount of silicate in the feedstock, expressed as SiO}_2}$$

of said process is less than or equal to 7, the separated and dried silica is ground, if necessary, until an average particle diameter $d_{50}$ from about 6 to about 13 μm is obtained.

2. The process according to claim 1, wherein the precipitated silica has a BET specific surface of about 70 to about 130 m²/g, an RDA abrasiveness from about 40 to about 80, a DOP oil uptake from about 120 ml/100 g to about 170 ml/100 g, and an SiO₂/M₂O ratio from about 3 to about 3.8.

* * * * *